United States Patent [19]
Gawarecki

[11] Patent Number: 6,142,152
[45] Date of Patent: Nov. 7, 2000

[54] COVER FOR AN OPERATING ROOM BACK TABLE

[75] Inventor: Herbert Gawarecki, Haltern, Germany

[73] Assignee: GFM Ingenieur - und Produktionstechnki GmbH, France

[21] Appl. No.: 09/151,478

[22] Filed: Sep. 8, 1998

[30] Foreign Application Priority Data

Sep. 15, 1997 [DE] Germany .................... 197 40 600

[51] Int. Cl.[7] .................................................. A61B 19/00
[52] U.S. Cl. ................................. 128/849; 128/852
[58] Field of Search ................................. 128/849–856; 206/438, 439, 440, 441

[56] References Cited

U.S. PATENT DOCUMENTS

| | | | |
|---|---|---|---|
| 3,724,651 | 4/1973 | Link | 206/56 AA |
| 3,942,523 | 3/1976 | Rudtke | 128/853 |
| 4,476,860 | 10/1984 | Collins | 128/852 |
| 5,170,804 | 12/1992 | Glassman | 128/849 |
| 5,174,306 | 12/1992 | Marshall | 128/852 |

*Primary Examiner*—Michael A. Brown
*Attorney, Agent, or Firm*—Renner, Kenner, Greive, Bobak, Taylor & Weber

[57] ABSTRACT

The invention concerns a back table cover (1) for an operating room back table with different surgical instruments (2) wrapped in it such as Mayo stand covers, operating room drapes, adhesive strips, napkins, stockings, etc that is encased in a packaging (26).

The invention is based on the problem of creating a table cover of the initially-cited kind in a quickly produced vacuum packaging (26) from which the table cover (1) can be removed undamaged and sterile with its surgical instrument set (2).

This problem is solved according to the invention in that the folded table cover (1) is provided with an air-permeable zone (17, 20, 29, 30, 34) leading to the interior from at least one of its outer areas (18, 18*a*).

14 Claims, 7 Drawing Sheets

COVER FOR AN OPERATING ROOM BACK TABLE

DESCRIPTION

The invention concerns a table cover (back table cover) for an operating room back table with different surgical instruments wrapped in it such as Mayo stand covers, operating room drapes, adhesive strips, napkins, stockings, etc. that are encased in a packaging.

Such a table cover in prior public use is placed on an operating room back table; the sterile table cover on the table is removed from a package with a peel seal and unfolded to cover the entire table. After it is unfolded, the sterile set of surgical instruments wrapped in it can be used for surgery. These sets of surgical instruments are for respective, specific operations and can hence vary quite a bit. The table cover in contrast always has specific standard dimensions.

The state-of-the-art package encasing the table cover with the enclosed set of surgical instruments consists of a deep-drawn plastic film with a cover-like peal seal that is opened by an OR nurse who has passed through a sterile lock. The table cover with its enclosed contents are then removed from the packaging. The prior-art packaging for such table covers contain air and are therefore correspondingly voluminous.

The essential disadvantage of the prior-art packaging of these table covers is that a break of the seal and hence non-sterile conditions of the packaging and its contents are identifiable by chance and not on an ad hoc basis. Since such table covers are only removed from the packaging while preparing for surgery which is frequently brief, the discovery of nonsterile packaging delays not just preparations but the operation itself since a new package can only be obtained through a corresponding sterile lock.

A table cover in a smaller package whose lack of seal can be immediately determined by hospital personnel could be created by a vacuum package. Since however such table covers with their packaging are manufactured a certain number of units per minute for economic reasons, only a very fast high-vacuum packaging system could be used. As initial tests have shown, however, the table cover inflates like a balloon and is partially or completely destroyed when the air is sucked out of its interior holding the enclosed set of surgical instruments.

This is where the invention comes into play. The invention is based on the problem of creating a table cover of the initially-cited kind in a quickly produced vacuum package that can be removed undamaged and sterile from the package with its set of surgical instruments.

This problem is solved according to the invention in that the folded table cover is provided with an air-permeable zone leading to the interior from at least one of its outer areas. It was surprisingly shown that a table cover with this design can be easily, safely and hygienically placed very quickly in packaging that is quickly evacuated using a low-pressure evacuation procedure.

The invention provides different embodiments for the air-permeable zone: In a first embodiment, the air-permeable zone is provided at a fold edge of the table cover. This embodiment allows a very wide-area channel that leads into the interior of the folded table cover.

In a second embodiment, the air-permeable zone is in the outside of the table cover. This design also allows large channels leading to the inside to evacuate the air in a correspondingly short time.

In a third embodiment, the air-permeable zone is between two folds of the table cover. The air-permeable zone in one advantageous embodiment can be formed either by a tube inserted between two folds and running to the interior, or by spacers creating the channel between the folds and extending into the interior of the table cover.

In one concrete embodiment, the air-permeable zone consists of slots introduced into the table cover that are either close to a fold edge or to the outside of the table cover. These slots are covered by a plastic film. The plastic film is advantageously glued, welded or embossed to the table cover at both ends of each slot and at the lengthwise side of the slots assigned to the inside of the table cover. This allows a path for evacuated air to flow specifically from the interior out to the encasing package with only a slight loss of flow, and the deflection angle of the air close to the slots does not exceed 90°.

In another concrete embodiment, the air-permeable zone consists of an opening in the outside of the folded table cover or an opening extending to a fold edge that is sealed by a membrane. The membrane is permeable to air from the inside to the outside and visa versa, but is impermeable to liquids and solids. The membrane can consist of Tyvek fleece or another fleece or a tissue. In this case, the membrane forms a diaphragm that lets the desired air flow from the inside outward and visa versa but blocks the penetration of liquids and solids.

This membrane is advantageously tightly adhered, welded or embossed at its outer edge to the edge of the opening of the table cover. "Tight" is this instance means sealed in both directions.

In the above-described examples, the air-permeable zone is always placed directly in the table cover. The invention also allows the possibility of creating an air-permeable zone without altering the table cover. Hence in one particularly advantageous development of the invention, the air-permeable zone consists of an air channel that is either formed by an inserted tube extending into the interior of the folded table cover, or by a channel formed by spacers between two folded layers and extending into the interior. Possible spacers are inserted rod-like bodies that are removed with the packaging.

In another advantageous embodiment of the invention, the air-permeable zone consists of an air channel that is formed by at least one interruption in an adhesive layer running parallel to a lengthwise side of the table cover in connection with the surfaces of the respective parts of the table cover adjacent to the interruption. The adhesive layer of the table cover is preferably between two separate plastic film parts reconnected by the adhesive layer, because the plastic of the table cover (usually polyethylene) can be easily glued in contrast to the tissue on it.

Several exemplary embodiments of the invention are portrayed in the drawings. Shown are:

FIGS. 13–15 Another embodiment of an air-permeable zone in the form of a tube inserted between the opposing surfaces of two folds, where FIG. 13 and 14 correspond to FIG. 5 and 6, and FIG. 15 is a view along arrow XV of FIG. 14, FIGS. 16–18 Another embodiment of an air-permeable zone in the form of spacers between two surfaces of two folded layers that create a channel leading into the interior; FIG. 16 corresponds to FIG. 6, and FIG. 17 corresponds to FIG. 5 while FIG. 18 represents the view along arrow 18 from FIG. 17.

FIG. 19 Perspective top view of another embodiment of an unfolded table cover with the set of surgical instruments to be folded inside and an adhesive layer with interruptions to create flow channels from the inside to the outside, FIG. 20 Enlarged section XX from FIG. 19, FIG. 21 View of the table cover from FIG. 19 after its lengthwise sides have been folded, and FIG. 22 Enlarged section XXII from FIG. 21.

In FIGS. 1–4, the table cover 1 consists of a green polyethylene film with an non-slip absorbent fleece 1a of the same color and a set of surgical instruments 2 in the middle that are to be folded in the table cover 1. This set of surgical instruments 2 can consist of completely different individual parts depending on the type of operation, e.g., a Mayo stand cover, operating room drapes, adhesive strips, napkins, stockings, etc. that are required for the respective operation.

Figure 1:
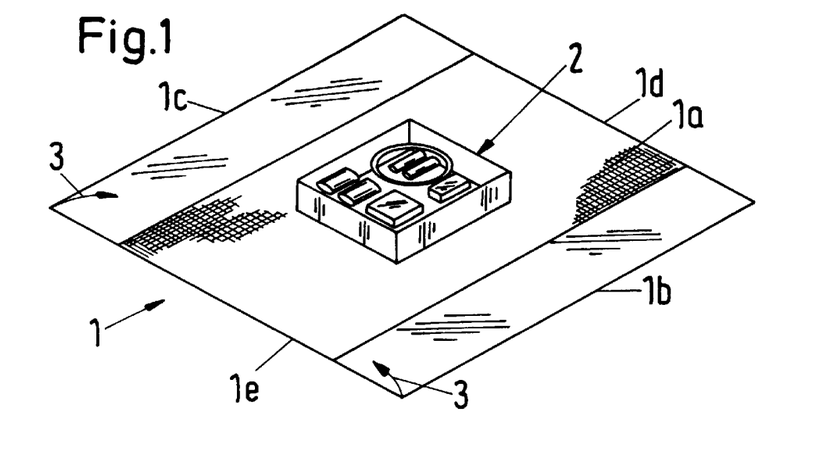
FIG. 1 A perspective top view of an unfolded back table cover for an OR back table on top of which are various surgical instruments that are to be wrapped up, FIG. 2 A perspective top view of the object from FIG. 1 folded lengthwise in the direction of the arrows in FIG. 1, FIG. 3 The folded table cover of FIG. 2 folded crosswise in the direction of the arrows in FIG. 2, FIG. 4 The table cover with its enclosed set of surgical instruments from FIG. 3 in a vacuum package, FIG. 5 Section along line V/V from FIG. 2 enlarged from FIG. 2, FIG. 6 Section along line VI/VI from FIG. 3 enlarged from FIG. 3, FIG. 7 Perspective top view of a folded table cover with its enclosed set of surgical instruments from FIG. 3 with a membrane on the outside to permit the passage of air during evacuation, FIG. 8 Enlarged section VIII from FIG. 7, FIG. 9 Section IX/IX from FIG. 8, FIG. 10 Perspective top view corresponding to FIG. 7 with several slots in the outside of the table cover that are covered by a film and are let air pass during evacuation, FIG. 11 Enlarged section XI from FIG. 10, FIG. 12 Section along line XII/XII from FIG. 11.
Figures 2, 3:
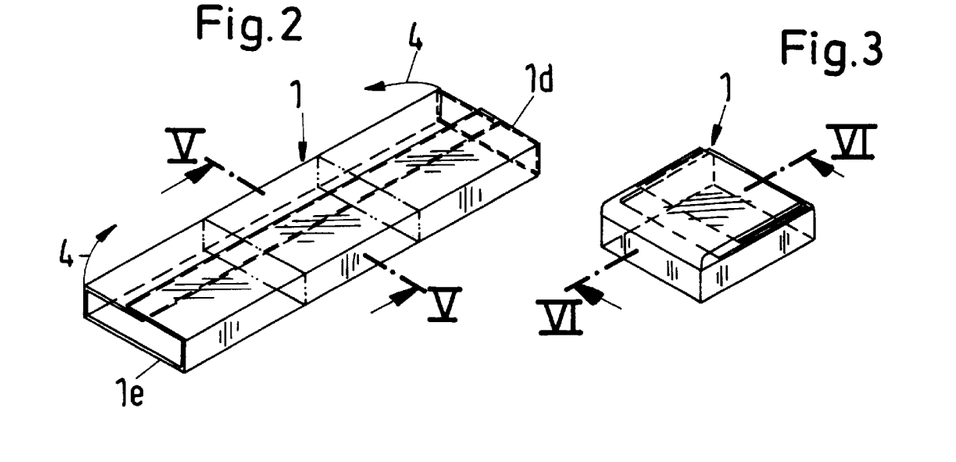
Figure 4:
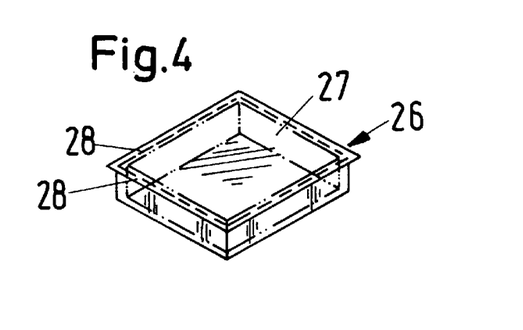
Figure 5:
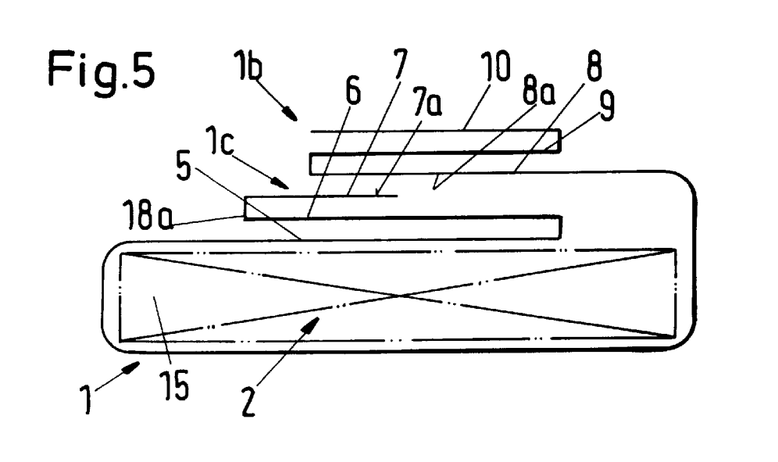

FIG. 2 shows the lengthwise sides 1b and 1c of the table cover 1 folded in the direction of arrows 3 from FIG. 1, and a cross section of the individual folded layers can be viewed in FIG. 5. The left folded side 1c has three folded layers 5, 6, and 7, and the right folded side 1b also has three folded layers 8, 9, and 10. The narrow sides 1b and 1e from FIG. 2 are folded in the direction of arrow 4. This fold is represented in a cross section in FIG. 6. The interior narrow side 1d has folded layers 11 and 12, and the outer narrow side 1e has folded layers 13 and 14.

Figure 6:
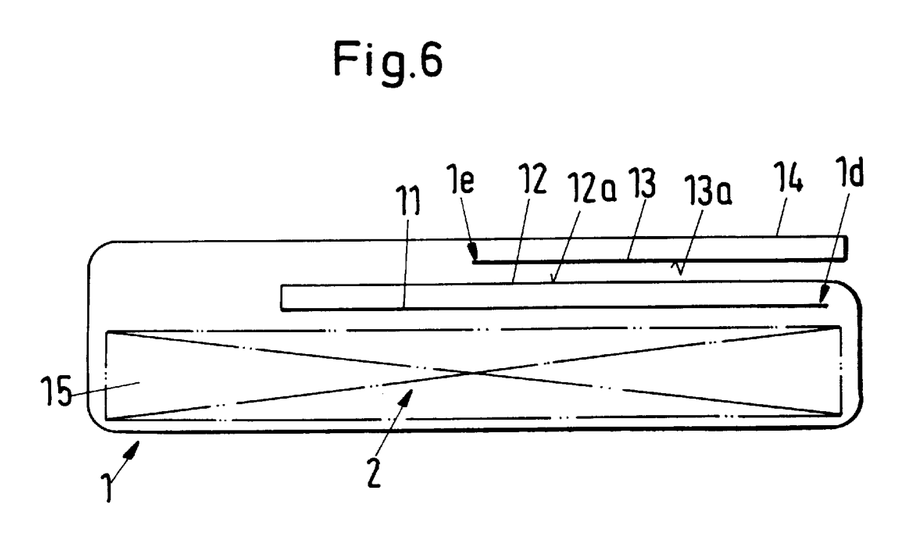

As can be seen in FIG. 5 and 6, the folded layers 7 and 8 form contact surfaces 7a and 8a in FIG. 5, and the facing folded layers 12 and 13 also form contact surfaces 12a and 13a in FIG. 6. Upon evacuating the air from the interior 15 of the folded table cover 1, they adhere so that the air to be withdrawn from the set of surgical instruments during evacuation will inflate the table cover 1 sealed by adhesion. This inflation process not only damages the table cover 1 itself but also the set of surgical instruments 2. To avoid this, the invention provides at least one of the outer areas of the folded table cover 1 with an air-permeable zone leading to the interior 15.

Figure 7:
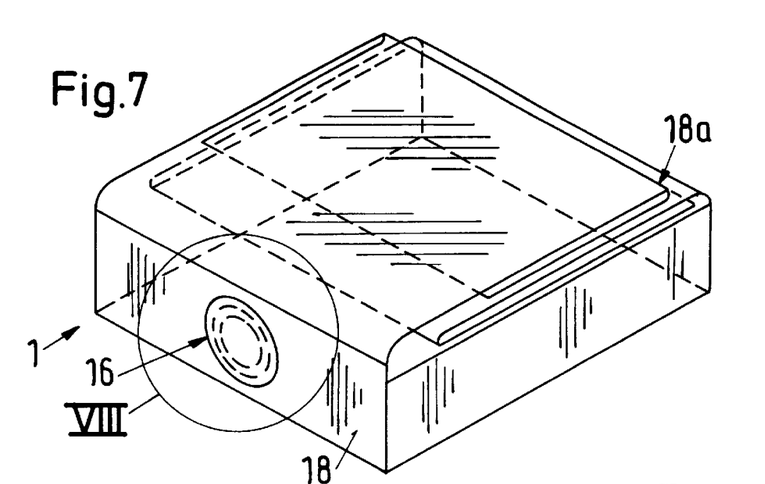
Figures 8, 9:
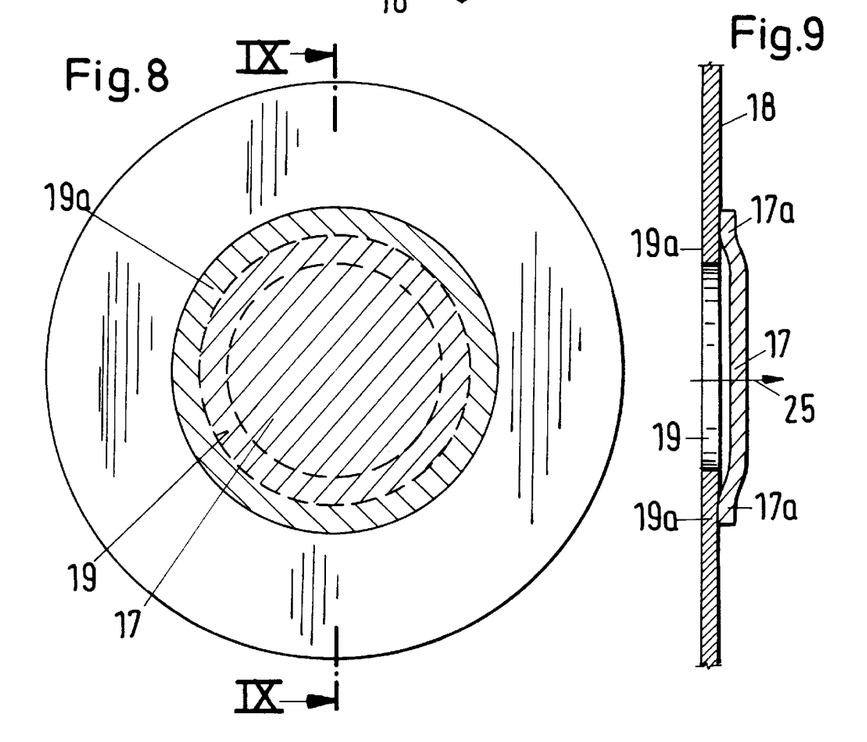

In a first embodiment according to FIGS. 7–9, this air-permeable zone 16 consists of a membrane 17 made of Tyvek fleece or another fleece or a tissue material that is on the outside 18 of the folded table cover in FIG. 7. As can be seen in FIG. 8 and 9, there is an opening 19 in the outside 18 of the table cover 1 that is sealed by the membrane 17. At the outer edge area 17a, the membrane 17 is tightly adhered, welded or embossed to the edge 19a of the opening 19 of the table cover 1. "Tight" in this instance means a seal to both sides.

Of course, the air-permeable zone 16 can be in a folded edge 18a (see FIGS. 5, 13, 14, 16, and 17).

In this manner, the function of the technical membrane as a diaphragm can be ensured which lets air pass from the inside 15 to the outside and visa versa but prevents moisture or solids from entering into the interior.

Figure 10:
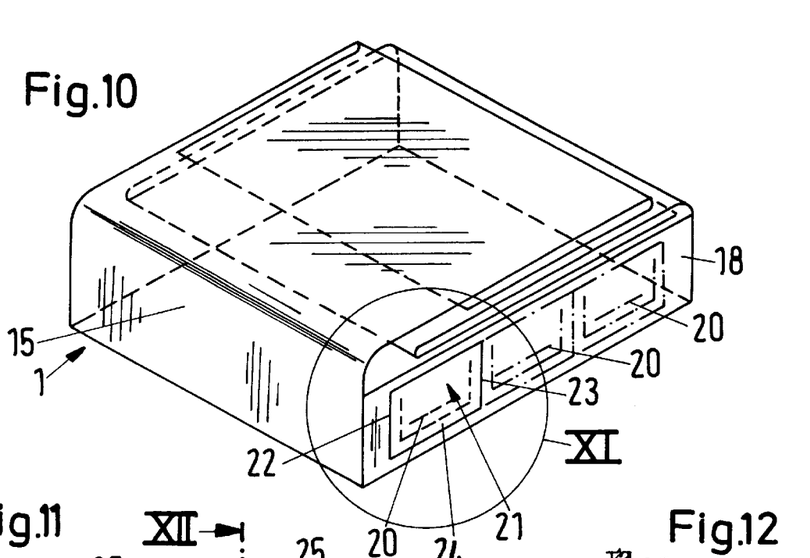
Figure 11:
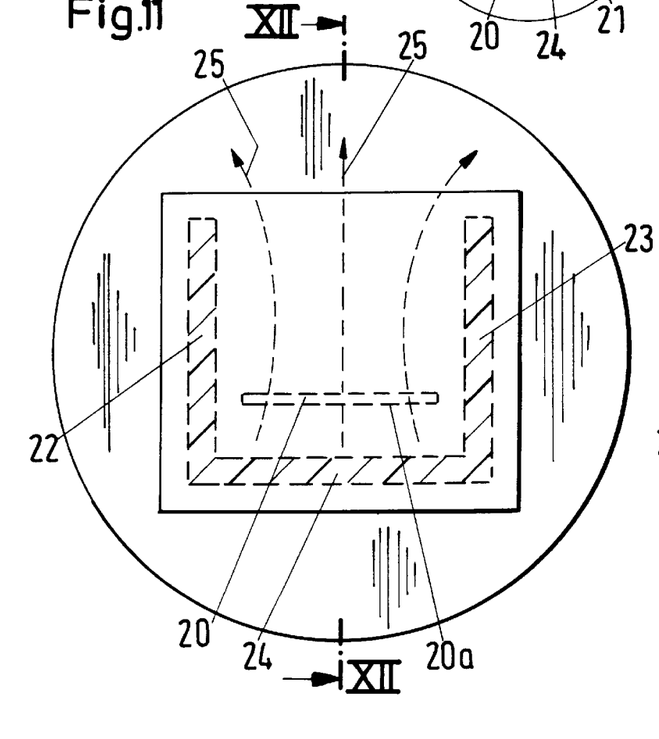
Figure 12:
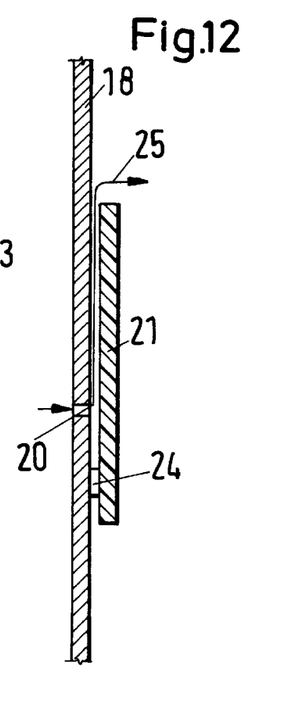

In FIGS. 10–12, the air-permeable zone consists of several slots 20 that are in an outer surface 18 of the folded table cover 1. These slots 20 are covered by a plastic film 21 that can be welded, adhered or embossed to the sides 22, 23 to the polyethylene film of the table cover 1, and to the lengthwise sides of the slot 20a assigned to the inside at 24. This allows the air to leave the interior 15 of the folded table cover 1 through the slot 20 in the direction of arrows 25 toward the encasing packaging 26 in FIG. 4. The cover 27 of this packaging 26 is connected to the packaging 26 with a peel connection 28. The arrows 25 also show the flow path of the air from the interior to the exterior in FIGS. 9, 14, 17, 18 and 21.

Figure 13:
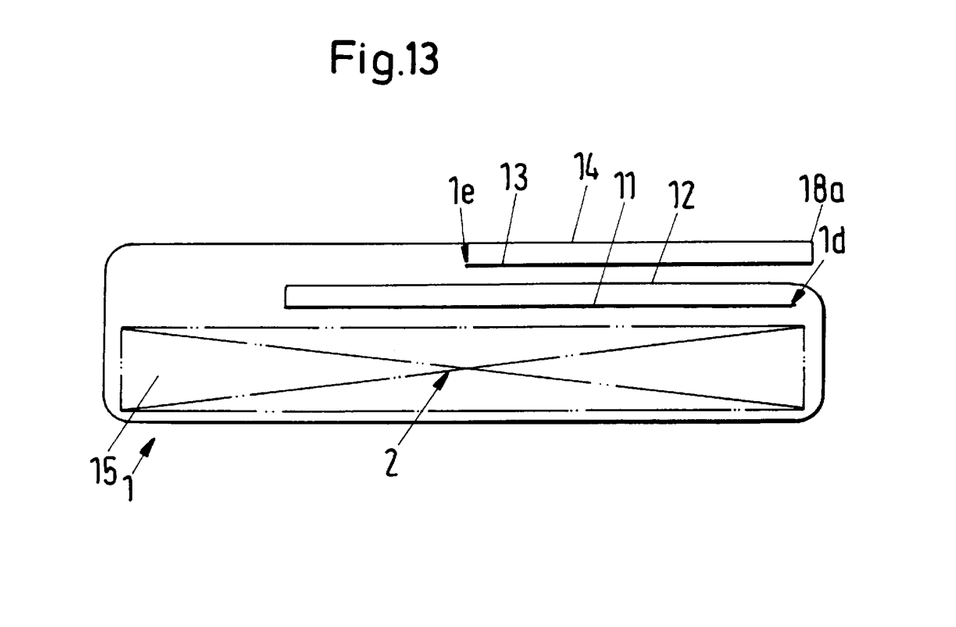
Figure 14:
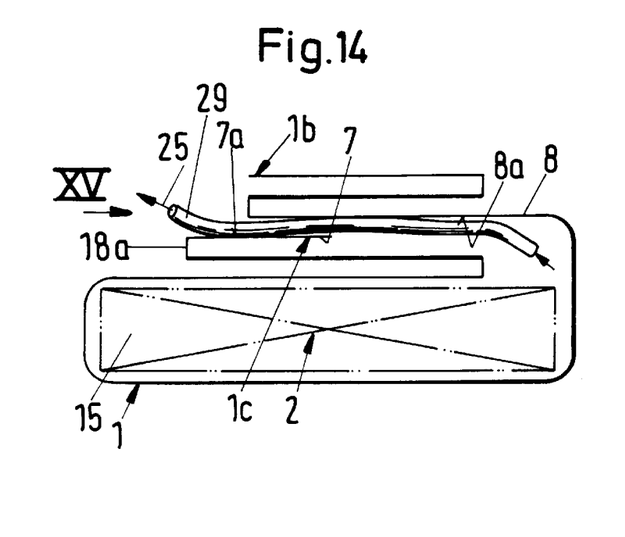
Figure 15:
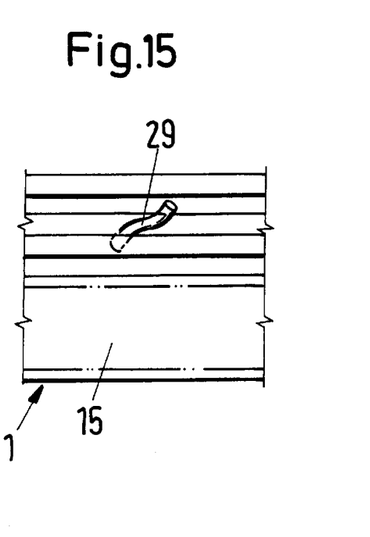

In FIGS. 13–15, the air-permeable zone consists of an air channel in the form of a tube 29 that is inserted between the contact surface 7a of folded layer 7 and the contact surface 8a of folded layer 8 (see FIG. 5), and it leads into the interior 15 of the folded table cover 1. Since the tube 29 is loosely placed between the folded layers 7 and 8, it is easy to remove from the packaging 26 when the folded table cover is removed from the packaging.

Figure 16:
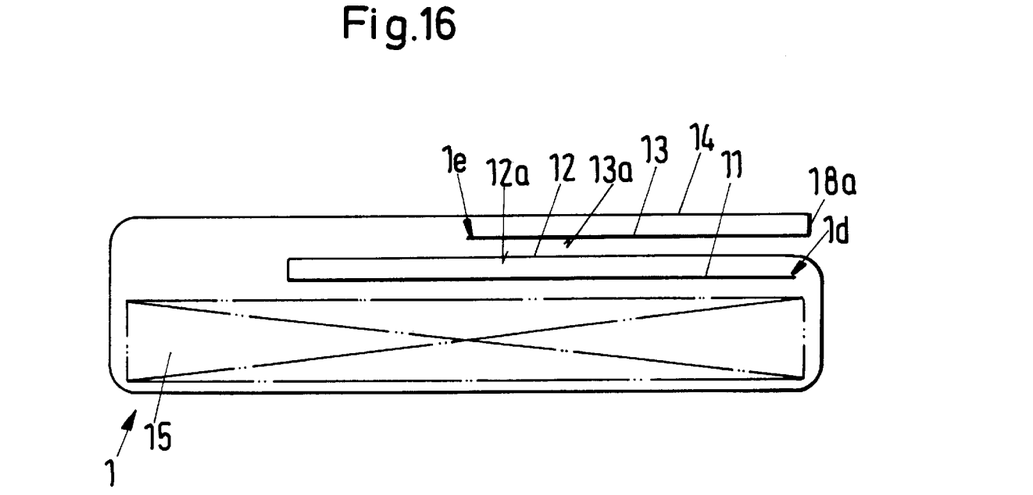
Figure 17:
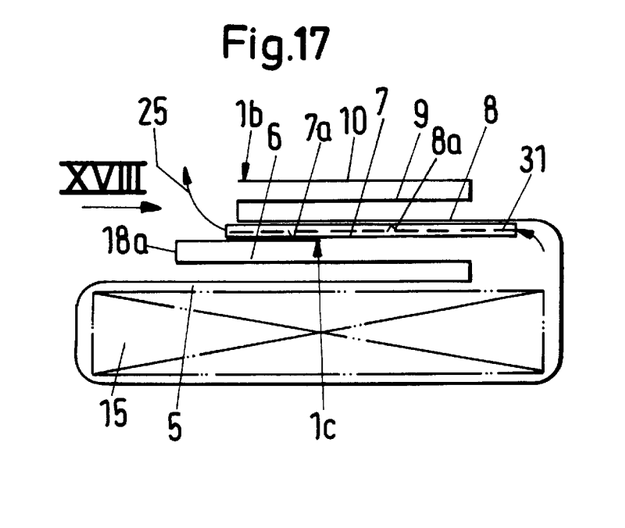
Figure 18:
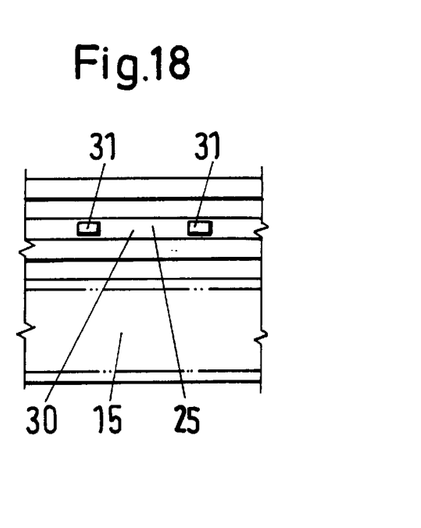

In FIGS. 16–18 is another air-permeable zone in the form of an air channel 30 that is formed by two spacers 31 and the adjacent folded layers (7 and 8 according to FIG. 5 along with FIG. 17). The channel 30 leads to the interior 15 of the folded table cover 1 as can be seen in FIGS. 17 and 18. The parts in FIGS. 6 and 13 that correspond are identified with the same reference numbers in FIG. 16. By means of the inserted spacer rods 31, the contact surfaces 7a and 8a of folded layers 7 and 8 are held at a distance from each other upon evacuation and cannot be "adhered" together from suction.

FIGS. 19–22 show another embodiment of the table cover 1 where an adhesive layer 32 with interruptions 33 is provided parallel to a lengthwise side 1b of the table cover 1. The interruptions 33 in the adhesive layer 32 form flow channels 34 together with the adjacent cover surfaces of the parts 35, 36 of the polyethylene film of the table cover 1 cut and then bonded with the adhesive layer 32. This allows air to pass outward during the evacuation process from the interior 15 of the folded table cover 1.

Figures 19, 20:
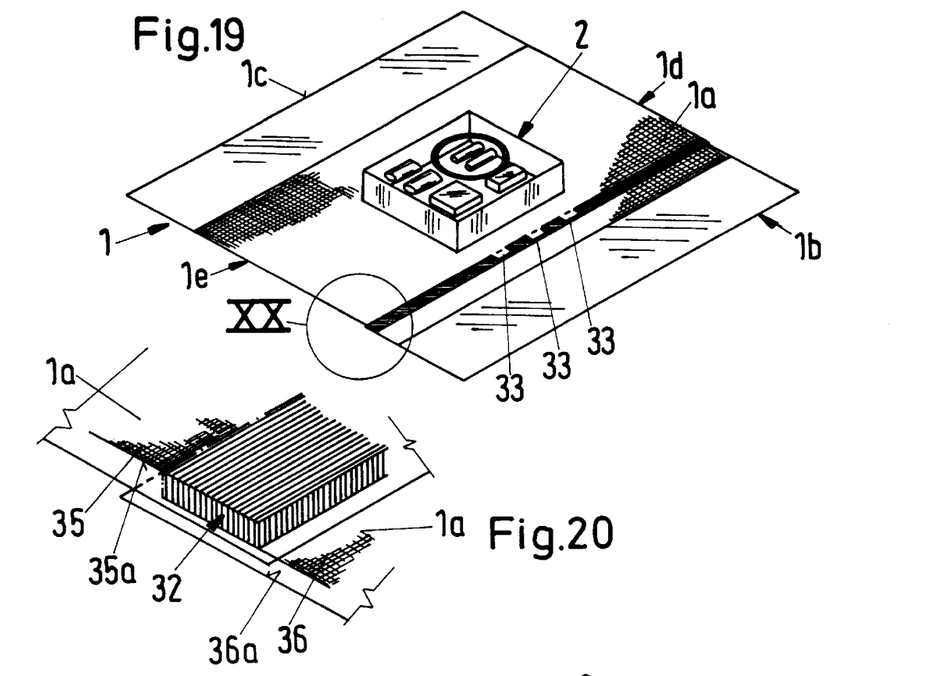

As FIG. 20 shows in connection with FIG. 19, the polyethylene film of the table cover 1 is divided into two parts 35 and 36 to effectively apply the adhesive layer 32 and then readhered by the adhesive layer 32 with its interruptions 33. The channels 32 are formed by the interruptions 33 in the adhesive layer 32 and the adjacent surfaces 35a, 36a of the cut parts 35, 36 of the polyethylene film of the table cover 1. In this manner, the interruptions 33 forming a part of the channels 34 can be continuously made in the table cover while producing the table cover 1.

Figures 21, 22:
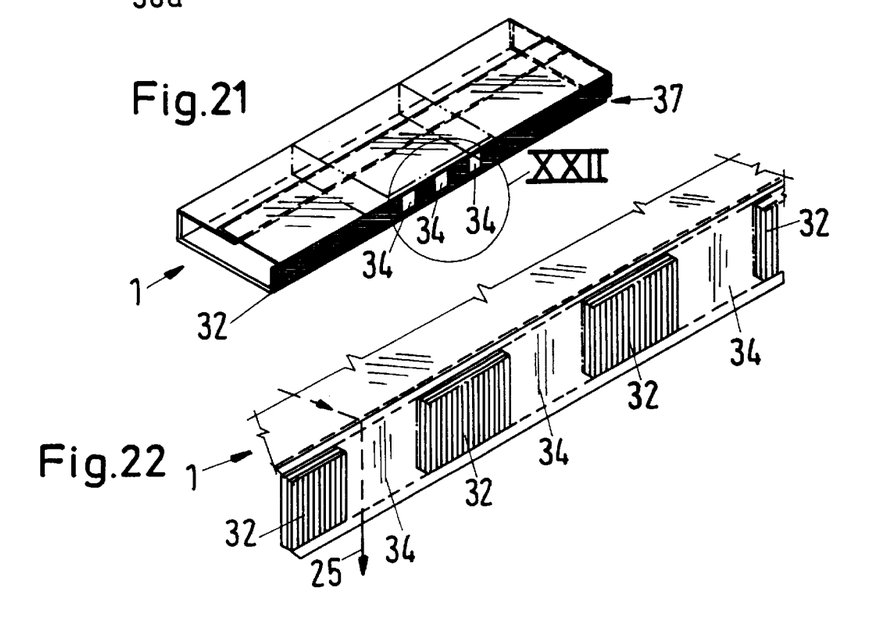

In FIGS. 21 and 22, it is particularly advantageous when the adhesive layer 32 with the channels is close to a lengthwise narrow side 37 after the fold of the lengthwise sides 1b and 1c of the table cover 1. In this manner, all the requirements for a satisfactory flow channel 34 are fulfilled.

REFERENCE NUMBER LIST

Table cover 1
Fleece 1a
Lengthwise sides of table cover 1 1b, 1c
Narrow sides of table cover 1 1d, 1e
Set of surgical instruments 2
Directional arrows for the direction of folding 3, 4
Folded layers 5, 6, 7, 8, 9, 11, 12, 13, 14
Contact surfaces of folded layers 7, 8; 12, 13 7a, 8a; 12a, 13a
Interior of the table cover 1 15
Air-permeable zone 16
Membrane 17
Outer edge area of membrane 17 17a
Outside of the folded table cover 1 18
Fold edge 18a
Opening in outside 18 19
Opening edge 19a
Slots 20
Lengthwise side of slots 20a
Plastic film 21
Adhesive strips of the plastic film 22, 23, 24
Arrows indicating air flow 25
Packaging 26
Cover of packaging 26 27
Peel seal 28
Tube 29
Air flow channels 30, 34
Spacers 31
Adhesive layer 32
Interruptions in the adhesive layer 32 33
Parts of cut polyethylene film of table cover 1 35, 36
Surfaces 35, 36 facing adhesive layer 32 35a, 36a

What is claimed is:

1. A liquid-impermeable and substantially air-impermeable back table cover for an OR back table with different enclosed surgical instruments such as Mayo stand covers, operating room drapes, adhesive strips, napkins, or stockings, that is encased by a packaging, wherein at least one of the outer areas of a folded table cover are provided with an air-permeable zone leading to the interior, said air-permeable zone serving to provide the table cover with the quality that it may be placed in packaging that can be quickly evacuated using a low-pressure evacuation procedure without the table cover inflating during such procedure.

2. A table cover according to claim 1 wherein the air-permeable zone is in a fold edge of the table cover.

3. A table cover according to claim 1 wherein the air-permeable zone is in the outside of the table cover.

4. A table cover according to claim I wherein the air-permeable zone is between two folded surfaces of the table cover.

5. A table cover according to one or more of claims 1–4 wherein the air-permeable zone consists of slots in the table cover that are covered by a plastic film.

6. A table cover according to claim 5 wherein the plastic film is adhered, welded or embossed to the table cover at the two ends of each slot and to the lengthwise slot side and to the lengthwise slot side assigned to the interior of the table cover.

7. A table cover according to one or more of claims 1–4 wherein the air permeable zone includes a membrane which is permeable to air from the inside to the outside and visa versa but is impermeable to liquids and solids.

8. A table cover according to claim 7 wherein the membrane consists of Tyvek fleece or another fleece or a tissue material.

9. A table cover according to claim 8 wherein the outer edges of the membrane are tightly glued, welded or embossed to the table cover.

10. A table cover according to one or more of claims 1–4 wherein the air-permeable zone consists of an air channel that is formed either by an inserted tube extending in the interior of the folded table cover or by a channel formed by spacers between surfaces of the folded layers and extending into the interior.

11. A table cover according to one or more of claims 1–4 wherein the air-permeable zone consists of an air channel that is formed by at least one interruption in an adhesive layer running parallel to a lengthwise side of the table cover or by a channel formed by spacers between surfaces of the respective folded layers adjacent to the interruption.

12. A table cover according to claim 11 wherein the adhesive layer of the table cover is between two separate plastic film parts that are reconnected by the adhesive layer.

13. A table cover according to one or more of claims 1–4 wherein the table cover is in a vacuum packaging.

14. A table cover according to claim 13 wherein the vacuum packaging has a peel seal on at least two side edges.

* * * * *